(12) United States Patent
Steinhardt et al.

(10) Patent No.: US 8,936,637 B2
(45) Date of Patent: Jan. 20, 2015

(54) VARIABLE-LENGTH PASSIVE OSSICULAR PROSTHESIS

(71) Applicant: Heinz Kurz GmbH Medizintechnik, Dusslingen (DE)

(72) Inventors: Uwe Steinhardt, Hirrlingen (DE); Thomas Lenarz, Hannover (DE); Axel Lang, Leonberg (DE); Heinz Kurz, Dusslingen (DE)

(73) Assignee: Heinz Kurz GmbH Medizintechnik, Dusslingen (DE)

( * ) Notice: Subject to any disclaimer, the term of this patent is extended or adjusted under 35 U.S.C. 154(b) by 0 days.

(21) Appl. No.: 13/633,932

(22) Filed: Oct. 3, 2012

(65) Prior Publication Data

US 2014/0094910 A1 Apr. 3, 2014

(30) Foreign Application Priority Data

Dec. 7, 2011 (DE) ..................... 20 2011 052 221 U

(51) Int. Cl.
*A61F 2/18* (2006.01)

(52) U.S. Cl.
USPC ............................................. 623/10; 600/25

(58) Field of Classification Search
CPC ....................................................... A61F 2/18
USPC ..................... 623/10, 11, 11.11; 600/25, 559; 607/55–57
See application file for complete search history.

(56) References Cited

U.S. PATENT DOCUMENTS

| 3,710,399 | A | 1/1973 | Hurst |
|---|---|---|---|
| 5,104,401 | A | 4/1992 | Kurz |
| 5,554,188 | A | 9/1996 | Prescott |
| 6,168,625 | B1 | 1/2001 | Prescott |
| 6,387,128 | B1 | 5/2002 | Kurz et al. |
| 6,554,861 | B2 | 4/2003 | Knox et al. |
| 7,226,406 | B2 | 6/2007 | Mueller et al. |
| 7,553,328 | B2 | 6/2009 | Steinhardt et al. |
| 8,105,229 | B2 | 1/2012 | Mueller et al. |
| 8,142,500 | B2 | 3/2012 | Steinhardt et al. |
| 2007/0083263 | A1 | 4/2007 | Steinhardt et al. |
| 2009/0149697 | A1 | 6/2009 | Steinhardt et al. |
| 2010/0191331 | A1* | 7/2010 | Steinhardt et al. .............. 623/10 |
| 2012/0078368 | A1 | 3/2012 | Lenarz et al. |

FOREIGN PATENT DOCUMENTS

| DE | 39 01 796 | 7/1990 |
|---|---|---|
| DE | 100 47 388 | 1/2002 |
| DE | 100 45 158 | 3/2002 |
| DE | 10 2005 010 705 | 8/2006 |
| DE | 10 2005 027 215 | 12/2006 |
| DE | 10 2005 048 618 | 4/2007 |
| DE | 10 2007 041 539 | 3/2009 |

(Continued)

*Primary Examiner* — Yashita Sharma
(74) *Attorney, Agent, or Firm* — Michael J. Striker

(57) ABSTRACT

A passive ossicular prosthesis includes a first and second fastening element for connection to the tympanic membrane. A connecting element connects the fastening elements in a sound-conducting manner. The connecting element includes a receiving part and an insertion part. The insertion part is inserted into a receiving opening of the receiving part. The receiving part encloses an end section of the insertion part in the manner of a clamp by way of two opposing, parallel legs disposed parallel to a shank axis of the connecting element. The legs have catch devices that fix the enclosed end section discrete spatial positions relative to the shank axis.

17 Claims, 5 Drawing Sheets

(56) References Cited

FOREIGN PATENT DOCUMENTS

| DE | 10 2009 016 468 | 12/2009 |
| DE | 10 2010 046 457 | 7/2011 |
| EP | 0 998 884 | 5/2000 |
| WO | 92/18066 | 10/1992 |
| WO | 02/069850 | 9/2002 |

* cited by examiner

VARIABLE-LENGTH PASSIVE OSSICULAR PROSTHESIS

CROSS-REFERENCE TO A RELATED APPLICATION

The invention described and claimed hereinbelow is also described in German Patent Application DE 20 2011 052 221.0, filed on Dec. 7, 2011. This German Patent Application, subject matter of which is incorporated herein by reference, provides the basis for a claim of priority of invention under 35 U.S.C. 119(a)-(d).

BACKGROUND OF THE INVENTION

The invention relates to a passive ossicular prosthesis that replaces or bridges at least one component of the human ossicular chain. Ossicular prostheses are known, for example, as disclosed in DE 10 2007 041 539 B4.

The human middle ear, comprising the ossicles thereof, has the function of transmitting the sound waves impacting the tympanic membrane via the external auditory meatus to the inner ear, which is filled with fluid. The three ossicles are the hammer (lat. malleus), which is fastened to the tympanic membrane, the stirrup (lat. stapes), which is connected via the footplate (lat. basis stapedis) thereof to the inner ear, and the anvil (lat. incus), which is located between the hammer and the stapes and is hingedly connected thereto. Hearing might not be possible without the human middle ear. For example, otosclerosis is a disease of the human petrosal bone (i.e., the bone in which the entire ear is seated), by which inflammation-like bone remodeling processes can result in fixation of the stapes, which normally swings freely. As a result, the sound signal is transmitted incompletely (or in some cases, not at all) via the ossicular chain to the inner ear, thereby resulting in hearing loss.

Ossicular prostheses are used to improve sound transmission in patients having different pathologies, for example, to conduct sound from the tympanic membrane to the inner ear in cases in which the ossicles of the human middle ear are missing or damaged, either entirely or partially. The ossicular prosthesis has two ends. Depending on the specific circumstances, one end of the ossicular prosthesis is fastened to the tympanic membrane, e.g. using a top plate, and the other end of the ossicular prosthesis is fastened (e.g. to the stapes of the human ossicular chain), or the ossicular prosthesis is inserted directly into the inner ear. In the known ossicular prostheses, sound conduction between the tympanic membrane and the inner ear is often limited as known ossicular prostheses cannot fully replace the natural anatomical formations of the ossicular chain.

Three types of ossicular prostheses used particularly frequently are stapes prostheses, partial prostheses, and total prostheses. Stapes prostheses are fixed to the incus and extend via a piston into the inner ear. Partial prostheses typically bear, via a top plate, against the tympanic membrane and establish a connection to the head of the stapes. Total prostheses connect the tympanic membrane to the base of the stapes.

One of the main problems that arise in every case of reconstructing the human ossicular chain involves selecting the correct length of the prosthesis. The lengths that are required vary within a range of several millimeters, due to differences in anatomy. When an ossicular prosthesis is surgically implanted, it is therefore necessary to have on hand a sufficiently large selection of prostheses having different axial lengths, or it must be possible to reduce the maximum starting length of the ossicular prostheses to the final axial length that is required.

WO 92/18066 A1 describes a self-adjusting ossicular prosthesis that comprises a spring mechanism in the connection between the first and second fastening elements, which makes it possible to continually change the axial length of the prosthesis depending on the relative position of the fastening points in the middle ear. Such self-adjusting ossicular prosthesis, however, is complicated and very costly to manufacture. It is therefore not possible to attain a fixed, reproducibly exact length of the prosthesis even though the length is retained after the prosthesis has been surgically implanted in the middle ear. In addition, due to its very special mechanical and geometric design, the known prosthesis requires a great deal of space in the middle ear, thereby rendering it entirely unusable in many cases due to the unique features of a particular patient. In addition, due to the design, a considerable amount of permanent pressure builds up between the two fastening points in the middle ear after implantation. This is known to limit healing after surgery, and often eventually results in postsurgical complications.

An ossicular prosthesis that has an axial length that may be varied within certain limits during surgery is described in DE 39 01 796 A1. In that case, the length is changed by bending the connecting element, which is designed as a thin gold wire. Accordingly, handling is complicated and relatively inaccurate thereby rendering it impossible to attain the desired exact axial length of the ossicular prosthesis. In addition, the result that is attained using this technique is not always reproducible and, once the connecting element has been bent, it is possible for the adjusted axial length of the ossicular prosthesis to change because the connecting element springs back.

EP 0 998 884 B1 describes an ossicular prosthesis in which the first connecting element (which is designed as an elongated shank) is inserted through a through-bore of the first fastening element (which is designed as a top plate) until a desired shank length between the first and second fastening elements is attained. The shank is then fixed in this position by constricting the through-bore in the top plate, and the section of the shank that extends past the top plate is trimmed off. One therefore easily obtains a prosthesis that has the particular length that is desired or required, and that remains exactly the same, after surgery in particular. A similarly acting construction is also known from DE 100 45 158 A1.

DE 10 2005 010 705 B3 makes known an ossicular prosthesis in which an intraoperative variability of the prosthesis length is attained by virtue of the fact that the elongated connecting element is designed in the form of a ball chain. During surgery, the ball chain is inserted through a receiving opening in the first fastening element via a certain number of balls. The ball chain is then fixed in the receiving opening of the fastening element using resilient web elements, which engage on either side of the ball chain but which, in contrast to the prosthesis described in DE 10 2007 041 539 B4, are not disposed along the shank axis, but rather transversely thereto in the plane of the first fastening element in the form of the tympanic membrane top plate. Said web elements, which function as a receiving part for the last ball, are therefore not even approximately capable of providing the ball chain, which functions as the insertion part. Therefore, the elongated connecting element, with positional stability in the direction of the shank axis, as is the case, approximately, with the two sections of the connecting element, can be displaced opposite one another coaxially with respect to the shank axis, according to DE 10 2007 041 539 B4.

In the ossicular prosthesis according to DE 10 2005 010 705 B3, the overhanging part of the ball chain that extends through the receiving opening is cut off before implantation in the middle ear, thereby ensuring that the prosthesis finally has exactly the desired axial length. Length variability is also attained in a similar manner in an ossicular prosthesis according to DE 10 2005 048 618 B4, in which a trimmable ball chain is likewise used as the connecting element, but wherein the receptacle in the first fastening element has a different design.

A further ossicular prosthesis having an intraoperatively variable axial length is described in U.S. Pat. No. 3,710,399. Therein, a two-piece connecting element is used between the two fastening elements; the two-piece connecting element comprises two parallel, straight wire pieces. One of the wire pieces extends away from the first fastening element and the second of the wire pieces extends away from the second fastening element. The two wire pieces may be connected to the particular other wire piece using wire loops at their ends, or they may be inserted into a type of connecting coupling having two parallel longitudinal bores for the two wire pieces. In the first case, it is not possible, however, to exactly adjust the fixing position and, therefore, the relative position of the two wire pieces. This makes it impossible to adjust the length of the prosthesis in an exact and reproducible manner. In the second case, once the wire pieces have been inserted into the connecting coupling, the relative positions of the wire pieces may tilt, flex, or become displaced, thereby likewise making it difficult or impossible to exactly adjust the axial length of the prosthesis.

Another technique for adjusting length is used with an ossicular prosthesis that is known from DE 10 2005 027 215 A1. The prosthesis is designed exclusively for use in the situation of stapes surgery, and so a plunger-shaped piston is always provided as the second fastening element. A receiving mechanism is located in this piston, into which the shank-shaped connecting element is inserted in the axial direction. Leaf springs that are spread radially apart by the connecting element have an arresting effect in a desired relative position between the connecting element and the second fastening element. Aside from the fact that an exactly reproducible adjustment of a desired axial length of the prosthesis is therefore not always guaranteed, the scope of application of this ossicular prosthesis is limited to surgery of the stapes, in the case of which a direct connection to the inner ear is attained via the piston. However, if a bell, piston, clip, or flat shoe is used as the second fastening part, for connection to another part of the ossicular chain, then this known prosthesis is not usable. If the intention is to form a related receiving mechanism in the second fastening part, then, due to geometry, it functions only in a piston and never in bell, flat shoe, or even in a clip.

An ossicular prosthesis described in U.S. Pat. No. 5,554,188 likewise comprises a connecting element that is designed as a two-piece shank. Therein, a first, rod-shaped section is inserted into a receiving bore of a second section, which is designed as a receiving part, and may be displaced axially in the bore. To attain a desired axial length of the prosthesis, the rod-shaped first section is trimmed from a maximum starting length to a suitable end length, and it is inserted into the second section until it stops. By designing the inner diameter of the receiving bore accordingly relative to the outer diameter of the first section, a frictional clamping of the first and second sections should bring about a certain fixation of the prosthesis length. The actual fixation is attained by virtue of the fact that the parts of the prosthesis that may move in opposite directions are unable to move very far apart from one another after surgical implantation in the middle ear, due to their being stopped at the two fastening points. It is therefore impossible to ensure, however, that a length of the prosthesis will always remain exactly the same.

A one-piece, variable-length ossicular prosthesis is known from DE 10 2009 016 468 B3. Therein, the adjustment device comprises at least two partial branches that extend symmetrically with respect to the longitudinal axis of the connecting element, are extendable and/or compressible in the axial direction, are permanently plastically deformable and are folded into multiple straps transverse to the longitudinal axis before deformation thereof.

In the ossicular prosthesis described in DE 10 2007 041 539 B4, the connecting element is designed to have a variable length in the axial direction between the receiving part and the insertion part. The specific axial length of the connecting element of an individual ossicular prosthesis is fixed by clamping the insertion part, including the receiving part, in a desired relative coaxial insertion position. The clamping force FK between the receiving part and the insertion part, in the clamped state, is at least 10 times greater, preferably approximately 100 times greater than the maximum external forces that occur naturally in the middle ear in the region of the ossicles. It is therefore possible to attain a desired, defined length of the prosthesis even before it is clamped between the two fastening points; this length is also fixedly retained after surgery, for example by inserting a second fastening element, which is designed as a piston, through a perforated base of the stapes. This makes it possible to attain a true variable length of the ossicular prosthesis "in situ" or intraoperatively in simple, low-cost manner.

A result is that large selections of prostheses having different lengths do not need to be kept on hand during every surgical procedure. In addition, it is particularly simple to adjust the particular length of the prosthesis that is desired, and, therefore, the handling is likewise particularly simple. The advantages of the above-described, known ossicular prosthesis according to U.S. Pat. No. 5,554,188 are utilized while retaining the advantages of the variable-length prostheses described in the above-mentioned, further documents and avoiding the common disadvantages. Due to the selection of the clamping force FK described, subsequent, postsurgical and undesired changes in length and/or position of the prosthesis are reliably prevented. In addition, said ossicular prosthesis may be used universally in all feasible types of couplings in the middle ear space, and it is not limited to a certain class of operations, while, for example, the prosthesis according to the above-mentioned document DE 10 2005 027 215 A1 may only be used exclusively in the situation of stapes surgery.

SUMMARY OF THE INVENTION

The present invention overcomes the shortcomings of known arts, such as those mentioned above.

The present invention improves a generic or known ossicular prosthesis to realize a prosthesis that is mechanically simpler than known prostheses and that ensures that the desired setting of the final position is obtained in a particularly precise and reproducible manner.

According to an embodiment, the invention includes a receiving part geometrically designed such that it encloses an end section of the insertion part in a non-positive and/or form-locked manner, in the manner of a clamp, by way of two opposing, substantially parallel legs disposed substantially parallel to the shank axis of the elongated connecting element. The two legs each comprise a catch device, which, upon interaction of the two legs, makes it possible to fix the enclosed end section in selectable, discrete spatial positions relative to the shank axis of the elongated connecting element. The catch devices of the legs of the receiving part comprise notches or indentations for receiving the end section, preferably in a form-locked manner, said notches or indentations being disposed, in the implanted state of the ossicular prosthesis, on inner surfaces bearing against the outer circumference of the end section and being disposed at opposing axial positions of the two legs. The notches or indentations are disposed on the inner surfaces of the two legs, equidistantly in the axial direction of each of the legs, which is particularly favorable in terms of production engineering.

The design of two parallel, clamp-type legs is known, per se, from DE 10 2010 046 457 B3, although in that case the two parallel, clamp-type legs are used exclusively in conjunction with an arrangement for adjusting and fixing the relative position between an actuator end piece of an active hearing implant and a component of the ossicular chain or a coupling part to the human inner ear. Such an active hearing implant has a completely different design, with the necessary electronics part and positioning thereof relative to the human middle ear, and functions in a completely different manner than a passive ossicular prosthesis of the type in question with respect to the present invention. The known use of the two parallel, clamp-type legs is therefore considered to be of a different type and would not prompt a person skilled in the relevant art to improve a passive ossicular prosthesis.

The clamp formed by the two legs in the ossicular prosthesis according to the invention is particularly easy to manufacture and is mechanically much more robust than the hollow receiving part that is used in the prosthesis of the type in question known from DE 10 2007 041 539 B4. The open design of the clamp also makes it easier to optically detect the position and the state of the insertion part within the receiving part and to easily correct them if necessary.

If the discrete axial clamping positions between the two legs are stepped with adequate geometric fineness, it is therefore possible to achieve an extremely exact spatial adjustment of the coupling point between the end section of the insertion part and the receiving part. This also considerably improves the possibility to spatially position and affix the desired position of the second fastening element relative to the first fastening element in the middle ear.

In a preferred embodiment of the invention, the connecting element comprises at least one joint, preferably a ball joint, in order to achieve increased flexibility and variability of the prosthesis. In terms of particularly high postsurgical mobility of the prosthesis, developments are advantageous in which a plurality of adjoining, further rotary elements are provided, preferably in the form of a ball joint chain.

Preferably, the receiving part is pivotably connected at the end thereof facing away from the two legs to the first fastening element by way of a ball joint.

Alternatively or in addition thereto, in other developments, the insertion part is pivotably connected at the end thereof facing away from the end section to the second fastening element by way of a ball joint.

Several degrees of freedom, in particular, with respect to the spatial adjustment of the prosthesis center part make an embodiment possible in which the connecting element comprises a plurality of receiving parts, each of which has substantially parallel legs enclosing an end section of an insertion part in the manner of a clamp. More particularly, in combination with the above-described embodiments comprising ball joints, the result is an endless number of geometric settings of the prosthesis upper part relative to the prosthesis lower part, thereby making it possible to intraoperatively adapt the ossicular prosthesis very precisely to the particular situation and to a specific shape of the middle ear region of the particular patient without the need to keep a large selection of differently shaped prostheses in various sizes on hand during every operation.

Preferably, the end section of the insertion part comprises an annular groove extending azimuthally on the outer circumference thereof, which is geometrically designed such that it fits as a counterpart to one of the notches or indentations of the catch devices of the two legs of the clamp-type receiving part. This ensures a particularly good and permanently stable fit of the arrangement after setting the desired relative final position of the first and second connecting elements. The insertion part is clamped with the receiving part continuously or in selectable discrete relative positions on an axial extension along the two legs, thereby making it possible to precisely set the desired prosthesis length in an individualized manner below the maximum length specified by the basic design of the prosthesis.

Variants in which the insertion part is clamped with the receiving part in a detent manner at the selected relative coaxial clamping position are particularly easy to handle, thereby enabling the prosthesis to remain permanently fixed at the desired, adjusted length and to be positioned between the fastening points in the middle ear.

In an embodiment, the insertion part of the ossicular prosthesis is passively clampable with the receiving part by way of inherent spring action upon interaction of the two legs of the receiving part.

Alternatively, the insertion part is designed to be actively clampable with the receiving part by way of external action on the two legs of the receiving part.

The insertion part also can be actively clamped by application of force from the outside, more particularly by way of the action of crimping tongs.

Also, the insertion part is actively clampable with the receiving part by application of heat to the ossicular prosthesis from the outside, for example, by heating the ossicular prosthesis to temperatures up to 90° C., preferably to body temperature.

A particularly advantageous embodiment includes that the insertion part and/or the receiving part are made of a material having a memory effect, more particularly of Nitinol. Although the use of materials of this type is known per se in the field of ossicular prostheses, it proves particularly effective in conjunction with the present invention.

Once the prosthesis is surgically implanted in the middle ear and the tympanic membrane is closed, the recovery phase begins. Scars form during this period, and they produce unforeseeable forces which can cause the prosthesis to move out of localized position thereof. When there is a stiff connection between the top plate and the shank, increased pressure peaks can result between the edge of the top plate and the tympanic membrane, or the graft between the tympanic membrane and the top plate. These pressure peaks can be so high that penetration or extrusion through the tympanic membrane would result. For this reason, it is very helpful for the prosthesis to have a certain amount of postsurgical mobility, so that the top plate may automatically adapt, postsurgically, to the position of the tympanic membrane. Since, in addition, the unique anatomical features of the ear vary (e.g., the position, shape and size of the stapes, incus, hammer and tympanic membrane), it is advantageous when ossicular prostheses are not designed to be rigid, but rather that they have a certain amount of flexibility or variability.

In some inventive embodiments, the first fastening element comprises a top plate designed to rest on the tympanic membrane. In other embodiments, the prosthesis is attached on one side, for example, to the limb of incus or to the stapes, or it may be inserted directly into the inner ear. In this context, an embodiment is advantageous in which the ossicular prosthesis is located at the end of the hammer (=umbo) or directly adjacent thereto, thereby resulting in the greatest leverage for the mechanical transmission of sound via motions that occur in the artificial or natural ossicular chain.

In some embodiments, the second fastening element is designed as a plate, a sleeve, a loop, a closed bell, a bell having one or two slots, or as a clip for mechanical connection to a further element of the ossicular chain.

Preferably, the prosthesis is fastened via the top plate to the tympanic membrane and via the second fastening element to the incus or stapes.

Alternatively, the ossicular prosthesis is coupled directly to the inner ear via the end thereof to which the second fastening element is attached via perforation of the stapes (stapedectomy or stapedotomy), and/or by opening up the human cochlea (=cochleotomy), more particularly via a second fastening element, which is designed as a piston.

In addition to the postsurgical shifting of position, a further problem results once ossicular prostheses have been implanted: The middle ear of the human body may be described as a "semi-open region". Any implantation material that is inserted in the body within the scope of reconstruction of the middle ear and its structures thereby undergoes a particular stress that predominates in a contaminated and infected environment, and which typically attacks the material. Since the objective of implanting an ossicular prosthesis must always be to enable the implant to remain in the patient's middle ear for as long as possible without complications occurring, a sustained attack on the material may result in damage being done to the prosthesis and/or in a local infection. Neither of these consequences is tolerable.

To that end, an embodiment of the invention includes that the surface of the ossicular prosthesis is coated entirely or at least in sections with a biologically active coating, in particular a growth-inhibiting and/or growth-promoting and/or antibacterial coating, in order to prevent damage from occurring to the implantation material or the surrounding tissue.

A first fastening element, which is designed as a top plate, of the ossicular prosthesis should always have a growth-promoting coating, but a second fastening element, which extends directly into the inner ear and is designed approximately in the form of a piston, also should have a growth-inhibiting coating.

The ossicular prosthesis or parts thereof is made of titanium and/or gold and/or tantalum and/or steel, and/or an alloy of said metals. It is known that titanium, in particular, in addition to being stiff and having excellent sound-conducting properties, also exhibits excellent biocompatibility with the human ear.

In terms of the postsurgical position adjustment described above, it is preferable that the prosthesis or parts thereof, in particular one of the fastening elements, are composed of a material having memory effect or superelastic properties. Nitinol in particular, as is known, for example, from WO 02/069850 A1 or U.S. Pat. No. 6,554,861 B2.

As an alternative, or in addition thereto, the parts of the ossicular prosthesis may be composed of a ceramic material.

The inventive prosthesis or parts thereof also may be made of biocompatible plastics, particularly silicone, polytetrafluoroethylene (PTFE), or fibrous composite materials. With these materials, postsurgical rejection reactions may also be prevented in most cases.

According to a preferred embodiment of the ossicular prosthesis, the mass distribution of the individual parts of the prosthesis is calculated depending on a desired, specifiable frequency response of sound conduction in the middle ear. This allows the sound propagation properties to be tuned to a certain extent using a custom-made ossicular prosthesis without a great deal of additional technical complexity.

Such "mechanical tuning" may be achieved, for example, by fastening at least one additional mass to a part of the ossicular chain or the prosthesis depending on a desired, specifiable frequency response of sound conduction in the middle ear. In one form, the additional mass is fastened to a part of the ossicular chain or the prosthesis using a clip. The additional mass and/or clip is preferably coated with a biologically active coating.

BRIEF DESCRIPTION OF THE DRAWINGS

Further features and advantages of the invention will become apparent from the description of embodiments that follows, with reference to the attached figures, wherein.

DETAILED DESCRIPTION OF THE PREFERRED EMBODIMENTS

Figure 1:
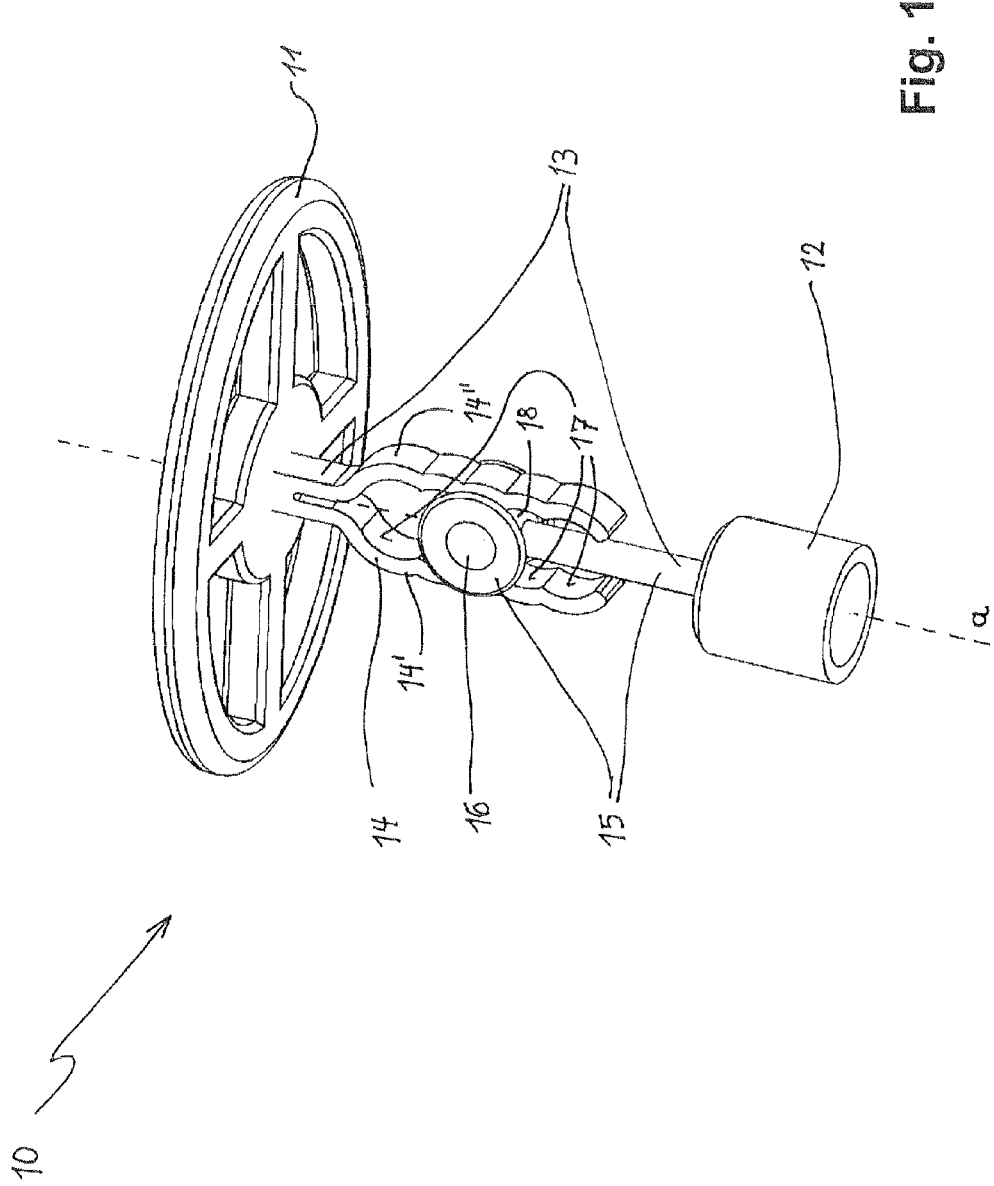
FIG. 1 depicts a schematic spatial depiction of an ossicular prosthesis according to the invention.

The following is a detailed description of example embodiments of the invention depicted in the accompanying drawings. The example embodiments are presented in such detail as to clearly communicate the invention and are designed to make such embodiments obvious to a person of ordinary skill in the art. However, the amount of detail offered is not intended to limit the anticipated variations of embodiments; on the contrary, the intention is to cover all modifications, equivalents, and alternatives falling within the spirit and scope of the present invention, as defined by the appended claims.

The drawing figures present four embodiments of the ossicular prosthesis 10; 20; 40; 50 according to the invention, using different levels of detail. Each ossicular prosthesis comprises, at one end, a first fastening element 11; 21; 41; 51. The first fastening element is used to mechanically connect the prosthesis to the tympanic membrane or a component of the ossicular chain. Attached to the other end of the ossicular prosthesis 10; 20; 40; 50 is a second fastening element 12; 22; 42; 52. The second connecting element mechanically connects the prosthesis to a further component or parts of a component of the ossicular chain, or for insertion directly into the inner ear.

Located between the first and second fastening elements is a connecting element 13; 23; 43; 53 in the form of an elongated shank, which connects the two fastening elements 11; 21; 41; 51 and 12; 22; 42; 52 to one another in a sound-conducting manner. The elongated shank comprises at least one first section, which is designed as a receiving part 14; 24; 44a, 44b; 54, and at least one second section, which is designed as an insertion part 15; 25; 45a, 45b; 55. The insertion part can be inserted into a receiving opening of a receiving part 14; 24; 44a, 44b; 54 and is clampable with the receiving part 14; 24; 44a, 44b; 54. The first fastening element 11; 21; 41; 51 is mechanically fixedly connected to one end and the second fastening element 12; 22; 42; 52 is mechanically fixedly connected to the axially opposed, other end of the connecting element 13; 23; 43; 53.

The receiving part 14; 24; 44a, 44b; 54 is geometrically designed such that it encloses an end section 16; 26; 46a, 46b; 56 of the insertion part 15; 25; 45a, 45b; 55 via two opposing, substantially parallel legs 14', 14"; 24',24"; 44a', 44a"; 44b', 44b"; 54',54" in a non-positive and/or form-locked manner, in the manner of a clamp. Accordingly, the two legs 14',14"; 24',24"; 44a', 44a"; 44b', 44b"; 54', 54" each have a catch device which makes it possible, upon interaction of the two legs 14',14"; 24',24"; 44a', 44a"; 44b', 44b"; 54', 54", for the enclosed end section 16; 26; 46a, 46b; 56 to be fixed in selectable, discrete spatial positions relative to the shank axis a of the elongated connecting element 13; 23; 43; 53.

The catch devices of the legs 14',14"; 24',24"; 44a', 44a"; 44b',44b"; 54',54" of the receiving part 14; 24; 44a, 44b; 54, on inner surfaces bearing on the outer circumference of the end section 16; 26; 46a, 46b; 56 in the implanted state of the ossicular prosthesis 10; 20; 40; 50, each comprise equidistantly disposed notches or indentations 17; 27; 47a, 47b; 57 for receiving the end section 16; 26; 46a, 46b; 56. The notches are disposed at opposite axial positions of the two legs 14', 14"; 24', 24"; 44a', 44a"; 44b',44b"; 54',54" parallel to the shank axis. The end section comprises an annular groove 18; 28; 48a, 48b; 58 extending azimuthally on the outer circumference thereof, which is geometrically designed such that it fits as a counterpart to one of the notches or indentations 17; 27; 47a, 47b; 57 of the catch devices of the two legs 14',14"; 24',24"; 44a', 44a"; 44b',44b"; 54',54" of the clamp-type receiving part 14; 24; 44a, 44b; 54.

In the embodiments shown, the insertion part 15; 25; 45a, 45b; 55 is passively clampable with the receiving part 14; 24; 44a, 44b; 54 by way of inherent spring action upon interaction of the two legs 14',14"; 24',24"; 44a', 44a"; 44b",44b"; 54',54" of the receiving part 14; 24; 44a, 44b; 54.

Alternatively or in addition thereto, the insertion part 15; 25; 45a, 45b; 55 can be actively clamped with the receiving part 14; 24; 44a, 44b; 54 by way of external action on the two legs 14',14"; 24',24"; 44a', 44a"; 44b',44b"; 54',54", for example, by application of force from the outside. Application of force from the outside may be imposed by way of the action of crimping tongs. Active clamping also may be implemented via application of heat to the ossicular prosthesis 10; 20; 40; 50 from the outside, for example, by heating to body temperature. It is very particularly advantageous in this case when the receiving part 14; 24; 44a, 44b; 54 and/or the insertion part 15; 25; 45a, 45b; 55 are made entirely or in part of a material having memory effect and/or superelastic properties, for example Nitinol.

Figure 2:
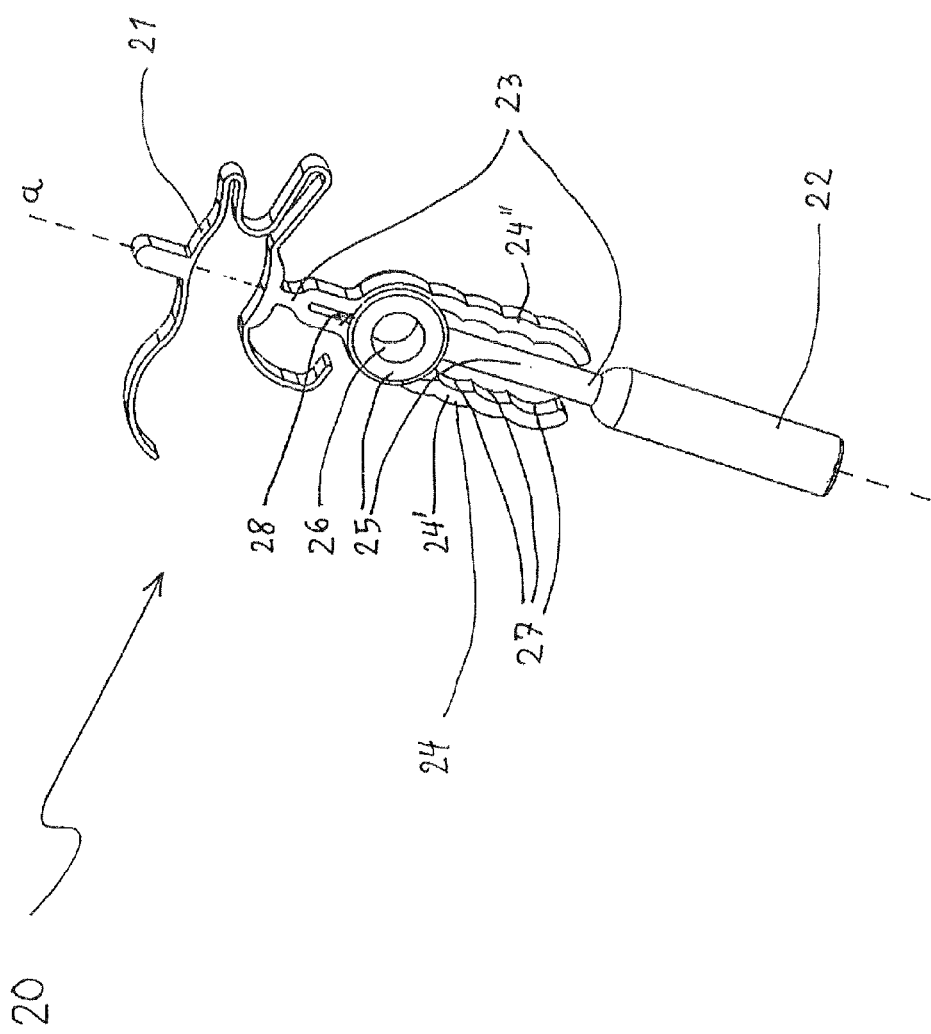
FIG. 2 depicts an ossicular prosthesis comprising a clip as the first fastening element and a piston as the second fastening element.
Figure 3:
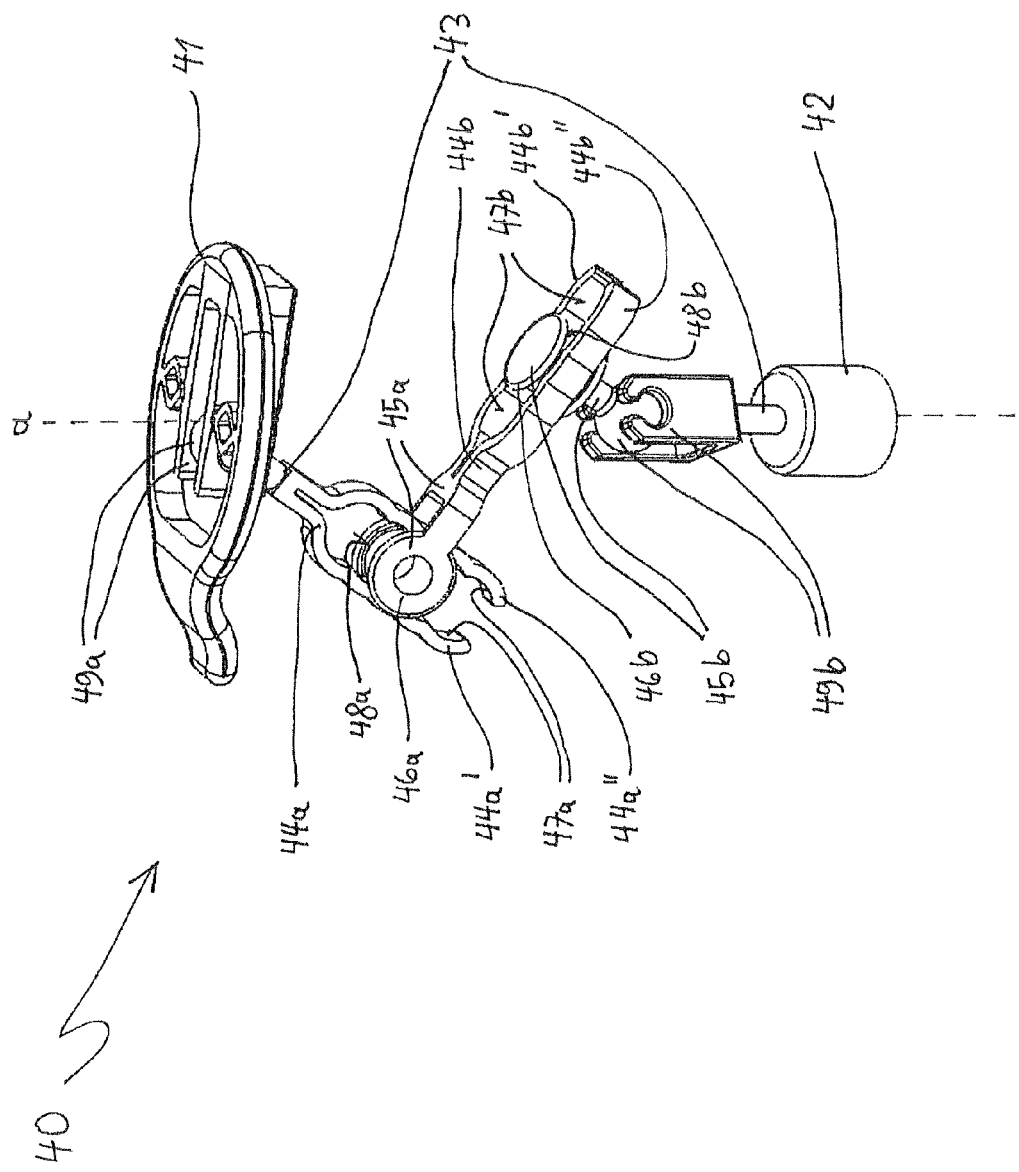
FIG. 3 depicts an ossicular prosthesis comprising a tympanic membrane top plate as the first fastening element and a piston-shaped second fastening element.

In the embodiments shown in FIGS. 1, 2 and 4, the two legs 14',14",24',24"; 54',54" of the receiving part 14; 24; 54 are disposed substantially parallel to the shank axis a of the elongated connecting element 13; 23; 53.

In the embodiment shown in FIG. 4, the connecting element 43 comprises a plurality of receiving parts 44a, 44b, each of which has substantially parallel legs 44a',44a"; 44b', 44b" enclosing an end section 46a, 46b of an associated insertion part 45a, 45b in the manner of a clamp. Moreover, a ball joint 49b is integrated in the connecting element 43 in order to attain a certain amount of postsurgical flexibility of the ossicular prosthesis 40 between the connection points thereof. The insertion part 45b is pivotably connected to the end thereof facing away from the end section 46b to the second fastening element 42 via the ball joint 49b. The receiving part 44a is pivotably connected via a further ball joint 49a at the end thereof facing away from the two legs 44a', 44a" to the first fastening element 41. The arrangement further increases the mobility of the prosthesis.

In the embodiment shown in FIG. 1, the first fastening element 11 is designed as a top plate for placement against the tympanic membrane. The second fastening element 12 is designed in the shape of a piston at the end opposite the top plate for placement against the base of the stapes. The latter also applies for the fourth embodiment (FIGS. 4a, 4b), comprising an ossicular prosthesis 40 wherein the first fastening element 41 is also in the form of a tympanic membrane top plate.

In the FIG. 2 embodiment, however, the first fastening element 21 is in the form of a clamp which may be clipped, for example, onto the limb of incus or to another component of the ossicular chain. The second fastening element 22 is designed as a piston for direct coupling of the ossicular prosthesis 20 to the inner ear.

Figure 4A:
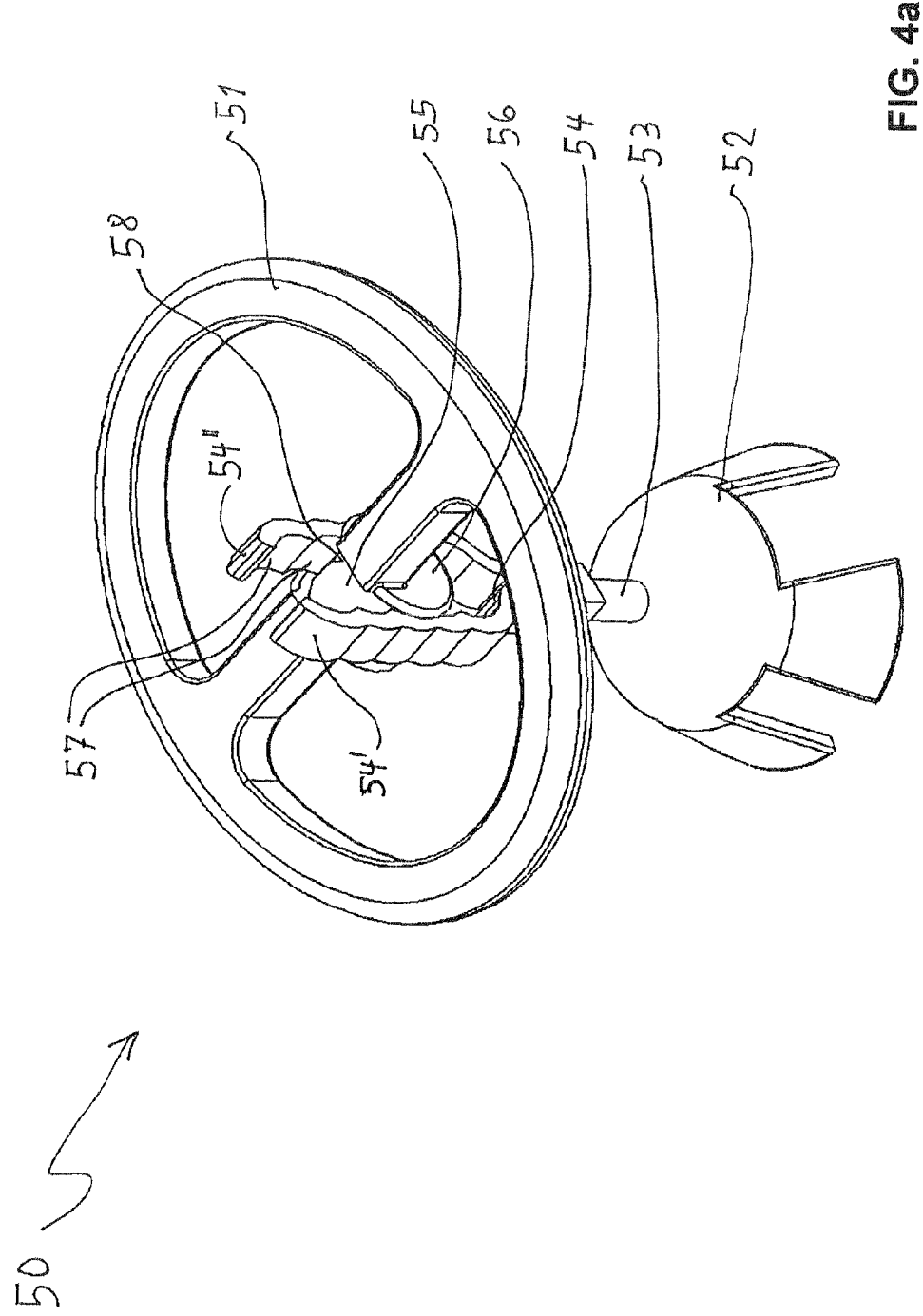
FIGS. 4a, 4b together depict an ossicular prosthesis comprising a tympanic membrane top plate as the first fastening element, a slotted bell as the second fastening element and a receiving part that is rigidly connected to the second fastening element.
Figure 4B:
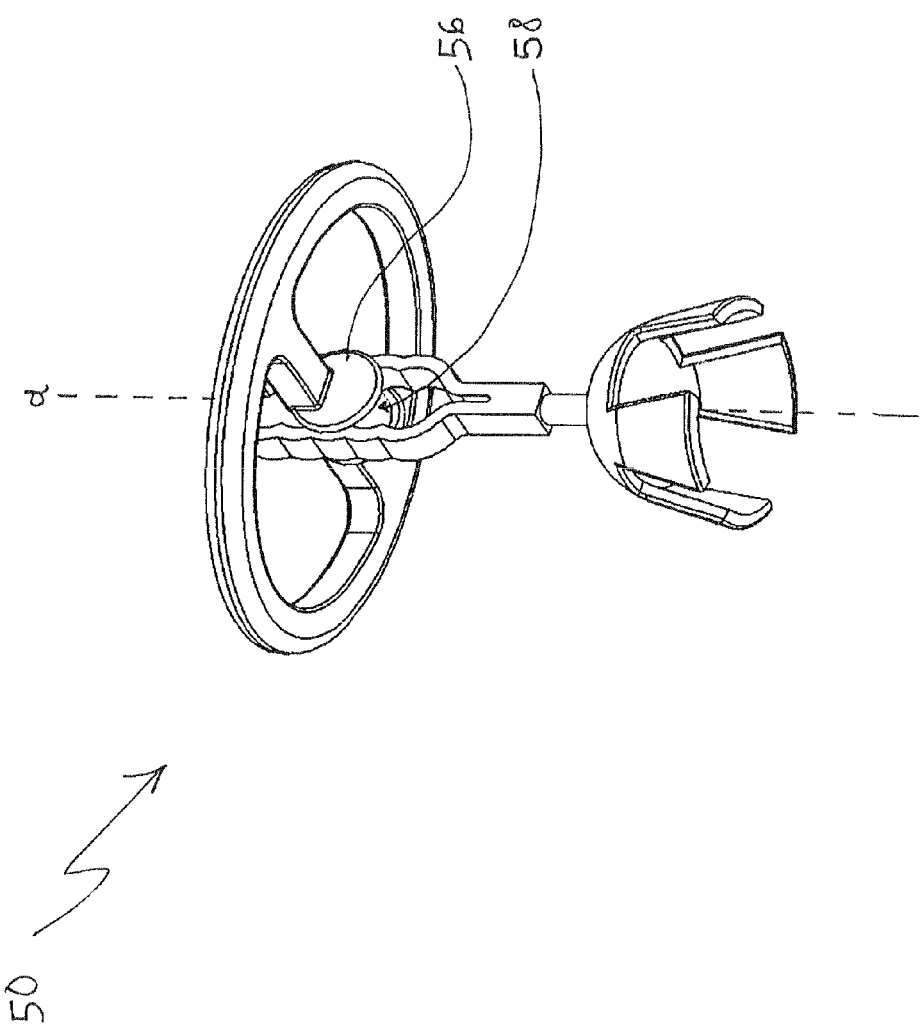

In the embodiment of FIGS. 4a, 4b, the first fastening element 51 also is a tympanic membrane top plate, while the second fastening element 52 is designed in the shape of a bell and used to attach the ossicular prosthesis 50 to the stapes. The receiving part 54 is rigidly connected to the second fastening element 52, while the insertion part 55, via the end section 56 thereof, is part of the first fastening element 51.

The mass distribution of the individual parts of the ossicular prosthesis 10; 20; 40; 50 may be calculated as a function of a desired, specifiable frequency response of sound conduction in the middle ear such that it is possible to tune the sound propagation properties in an individualized manner. This can also be achieved by way of trimming masses that can be clipped to the ossicular prosthesis in embodiments of the invention that are not depicted in the drawings.

As will be evident to persons skilled in the art, the foregoing detailed description and figures are presented as examples of the invention, and that variations are contemplated that do not depart from the fair scope of the teachings and descriptions set forth in this disclosure. The foregoing is not intended to limit what has been invented, except to the extent that the following claims so limit that.

What is claimed is:

1. A passive ossicular prosthesis for replacing or bridging at least one component of the human ossicular chain, passive ossicular prosthesis comprising:
 a first end and a second end axially displaced from the first end;
 a first fastening element provided at the first end for mechanical connection to the tympanic membrane or a component of the ossicular chain;
 a second fastening element provided at the second end for mechanical connection to a further component, or parts of a component, of the ossicular chain;
 an elongated connecting element forming an interconnection with the two fastening elements in a sound-conducting manner, the elongated connecting element comprising a first section in the form of a receiving part along a shank axis of the elongated connecting element and a second section in the form of an insertion part for insertion into a receiving opening of the receiving part and which is clampable with the receiving part, wherein the interconnection includes that first fastening element is mechanically rigidly connected to one end of the elongated connecting element and the second fastening element is mechanically rigidly connected to the other, axially opposed, end of the connecting element, wherein the receiving part is geometrically designed to enclose an end section of the insertion part in a non-positive or form-locked manner by way of two opposing, substantially parallel legs disposed substantially parallel to the shank axis of the elongated connecting element, each of which of the two legs comprising a catch device and which together interact to fix the enclosed end section in selectable, discrete spatial positions relative to the shank axis of the elongated connecting element for providing length variability to the passive ossicular prosthesis, wherein the catch devices each comprise notches or indentations for receiving the end section and which are disposed, in the implanted state of the ossicular prosthesis, on inner surfaces bearing against an outer circumference of the end section, said notches and indentations disposed on the inner surfaces of the two legs at opposing axial positions equidistantly in the axial direction of each of the legs.

2. The ossicular prosthesis according to claim 1, wherein the connecting element comprises at least one joint, wherein the joint is a ball joint.

3. The ossicular prosthesis according to claim 2, wherein the receiving part is pivotably connected at an end thereof facing away from the two legs to the first fastening element by way of a ball joint.

4. The ossicular prosthesis according to claim 2, wherein the insertion part is pivotably connected at an end thereof facing away from the end section to the second fastening element by way of a ball joint.

5. The ossicular prosthesis according to claim 1, wherein the connecting element comprises a plurality of receiving parts, each of which has substantially parallel legs enclosing an end section of an insertion part in the manner of a clamp.

6. The ossicular prosthesis according to claim 1, wherein the end section of the insertion part comprises an annular groove extending azimuthally on the outer circumference thereof, which annular groove is geometrically designed such that it fits as a counterpart to one of the notches or indentations of the catch devices of the two legs of the clamp-type receiving part.

7. The ossicular prosthesis according to claim 1, wherein the insertion part is passively clampable with the receiving part by way of inherent spring action upon interaction of the two legs of the receiving part.

8. The ossicular prosthesis according to claim 1, wherein the insertion part is actively clampable with the receiving part by way of external action on the two legs of the receiving part.

9. The ossicular prosthesis according to claim 8, wherein the insertion part is actively clamped by application of force from the outside.

10. The ossicular prosthesis according to claim 9, wherein the application force is applied by action of crimping tongs.

11. The ossicular prosthesis according to claim 8, wherein the insertion part is actively clampable with the receiving part by application of heat to the ossicular prosthesis from the outside.

12. The ossicular prosthesis according to claim 11, wherein the ossicular prosthesis is heated to temperatures up to 90° C.

13. The ossicular prosthesis according to claim 11, wherein the receiving part or the insertion part or both are made entirely or partially of a material having memory effect or having superelastic properties or both.

14. The ossicular prosthesis according to claim 13, wherein the material comprises Nitinol.

15. The ossicular prosthesis according to claim 1, wherein the first fastening element is configured to be attached to the limb of incus or the manubrium of malleus.

16. The ossicular prosthesis according to claim 1, wherein the second fastening element is configured to be attached directly to the inner ear.

17. The ossicular prosthesis according to claim 1, wherein the non-positive or form-locked manner operate to clamp.

* * * * *